(12) United States Patent
Ye et al.

(10) Patent No.: US 10,101,301 B2
(45) Date of Patent: Oct. 16, 2018

(54) ROTATING FIELD TRANSCEIVER NONDESTRUCTIVE INSPECTION PROBE

(71) Applicant: BOARD OF TRUSTEES OF MICHIGAN STATE UNIVERSITY, East Lansing, MI (US)

(72) Inventors: Chaofeng Ye, Lansing, MI (US); Satish S. Udpa, Okemos, MI (US); Lalita Udpa, Okemos, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 0 days.

(21) Appl. No.: 15/076,158

(22) Filed: Mar. 21, 2016

(65) Prior Publication Data

US 2016/0282307 A1 Sep. 29, 2016

Related U.S. Application Data

(60) Provisional application No. 62/137,493, filed on Mar. 24, 2015.

(51) Int. Cl.
*G01N 27/90* (2006.01)
(52) U.S. Cl.
CPC ....... *G01N 27/9033* (2013.01); *G01N 27/904* (2013.01); *G01N 27/9046* (2013.01)
(58) Field of Classification Search
CPC ............. G01N 27/9046; G01N 27/904; G01N 27/9033; G01N 27/902; G01N 27/90
USPC ....................................................... 324/222
See application file for complete search history.

(56) References Cited

U.S. PATENT DOCUMENTS

| 2,806,992 | A | * | 9/1957 | Foerster | ................. | G01N 27/90 |
| | | | | | | 324/239 |
| 3,483,466 | A | * | 12/1969 | Beaver | ................. | G01N 27/904 |
| | | | | | | 324/220 |
| 4,856,337 | A | * | 8/1989 | Metala | ................. | G01N 27/902 |
| | | | | | | 324/220 |
| 5,256,966 | A | * | 10/1993 | Edwards | .............. | G01N 27/904 |
| | | | | | | 324/220 |
| 6,249,119 | B1 | * | 6/2001 | Curtis, Jr. | ............. | E21B 17/006 |
| | | | | | | 324/227 |
| 6,384,592 | B1 | * | 5/2002 | Sylvester | ................. | G01R 7/06 |
| | | | | | | 324/144 |
| 6,456,066 | B1 | * | 9/2002 | Burd | .................... | G01N 27/902 |
| | | | | | | 324/220 |

(Continued)

OTHER PUBLICATIONS

Xin, Junjun, et al. "Rotating field eddy current probe with bobbin pickup coil for steam generator tubes inspection." Ndt & E International 54 (2013): 45-55.*

(Continued)

*Primary Examiner* — Christopher McAndrew
(74) *Attorney, Agent, or Firm* — Marshall, Gerstein & Borun LLP

(57) ABSTRACT

A rotating magnetic field probe includes three (or more) windings that work in both transmit and receive mode, to form an eddy current detection transceiver. In a transmit mode, the windings are driven with a drive signal (e.g., an alternating current) having similar or the same magnitude at each winding, but differing in phase from one another. In a receive mode, the terminal voltages of the windings is measured and summed to determine the location of a defect.

9 Claims, 6 Drawing Sheets

(56) References Cited

U.S. PATENT DOCUMENTS

| | | | | |
|---|---|---|---|---|
| 7,434,485 | B2* | 10/2008 | Hunter | G03F 7/707 73/865.9 |
| 7,622,916 | B2* | 11/2009 | Meeten | G01N 27/72 324/220 |
| 8,928,315 | B2* | 1/2015 | Hashimoto | G01N 27/902 324/220 |
| 9,203,500 | B2* | 12/2015 | Danak | H04B 1/40 |
| 9,267,921 | B2* | 2/2016 | Michaeu-Cunningham | G01N 27/9033 |
| 9,316,617 | B2* | 4/2016 | Graebner | G01N 27/902 |
| 9,450,637 | B2* | 9/2016 | Manssen | H03H 7/40 |
| 2001/0045840 | A1* | 11/2001 | Cirkel | G01R 31/2884 324/750.3 |
| 2004/0263158 | A1* | 12/2004 | Biester | E21B 47/0905 324/207.24 |
| 2007/0222413 | A1* | 9/2007 | Kinoshita | B60L 11/1868 320/104 |
| 2009/0273342 | A1* | 11/2009 | Drummy | G01N 27/90 324/238 |
| 2011/0163741 | A1* | 7/2011 | Suzuma | G01N 27/9013 324/240 |
| 2013/0009634 | A1* | 1/2013 | Lakhan | B24B 49/105 324/229 |
| 2014/0002070 | A1* | 1/2014 | Michaeu-Cunningham | G01N 27/902 324/240 |
| 2014/0076872 | A1* | 3/2014 | Ott | B23K 9/1087 219/132 |
| 2014/0113679 | A1* | 4/2014 | Wehrmann | H04B 1/0458 455/550.1 |
| 2014/0120849 | A1* | 5/2014 | Peltonen | H04B 1/40 455/77 |
| 2014/0184335 | A1* | 7/2014 | Nobbe | H03F 1/0227 330/291 |
| 2014/0184336 | A1* | 7/2014 | Nobbe | H03F 1/0227 330/296 |
| 2014/0184337 | A1* | 7/2014 | Nobbe | H03F 1/0227 330/296 |
| 2014/0199949 | A1* | 7/2014 | Nagode | H03F 1/0227 455/73 |
| 2014/0378076 | A1* | 12/2014 | Manssen | H03H 7/40 455/77 |

OTHER PUBLICATIONS

Xin, Junjun, et al. "Nondestructive inspection using rotating magnetic field eddy-current probe." IEEE Transactions on Magnetics 47.5 (2011): 1070-1073.*

Capobianco, "Rotating Field Eddy Current Probe for Characterization of Cracking in Non-Magnetic Tube," Technique Report (1998).

Grimberg, et al. "Inner-Eddy-Current Transducer with Rotating Magnetic Field, Experimental Results: Application to Nondestructive Examination of Pressure Tubes in PHWR Nuclear Power Plants," Research in Nondestructive Evaluation, 16(2):65-77 (2005).

Grimberg, et al., "Inner-Eddy-Current Transducer with Rotating Magnetic Field: Theoretical Model," Research in Nondestructive Evaluation, 16(2):79-100 (2005).

Karthik et al., "Finite element optimization for nondestructive evaluation on a graphics processing unit for ground vehicle hull inspection," Modeling & Simulation, Testing and Validation (MSTV) Mini-Symposium Aug. 2013.

Karthik, et al. "Faster, more accurate, parallelized inversion for shape optimization in electroheat problems on a graphics processing unit (GPU) with the real-coded genetic algorithm," The International Journal for Computation and Mathematics in Electrical and Electronic Engineering, 34(1):344-356 (2015).

Lafontaine, et al. "Eddy Current Array Probes for Faster, Better and Cheaper Inspections," NDT.net, 5(10): (2000).

Sivasuthan, et al. "A Script-based, parameterized finite element mesh for design and NDE on a GPU." IETE Technical Review 32(2):94-103 (2015).

Zeng, et al. ""Reduced Magnetic Vector Potential Formulation in the Finite Element Analysis of Eddy Current Nondestructive Testing, IEEE Trans Magn, 45(3):964-967 (2009).

Zeng, et al. "Finite-Element Model for Simulation of Ferrite-Core Eddy-Current Probe," IEEE Trans Magn, 46(3)905-909 (2010).

* cited by examiner

ROTATING FIELD TRANSCEIVER NONDESTRUCTIVE INSPECTION PROBE

CROSS-REFERENCE TO RELATED APPLICATIONS

This application claims the benefit of U.S. Provisional Application Ser. No. 62/137,493, filed Mar. 24, 2015, entitled "Rotating Field Transceiver Nondestructive Inspection Probe" the entirety of which is hereby incorporated herein by reference.

FIELD OF THE INVENTION

The present disclosure relates generally to detecting defects in environmentally isolated vessels (tubing, etc.) that transport gases and fluids and, more particularly, to eddy current defect detectors.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

A variety of eddy current probes have been developed for inspecting nuclear power plant steam generator tubes over the last few decades. Commercial probes such as bobbin coil probes (absolute and differential modes), rotating probes (Rotating Pancake Coil and Plus-Point), and array probes (X-Probe, Smart Array Probe and Intelligent Probe) have been used extensively in industry.

While these probes are commonplace, they are limited in operation. Conventional bobbin coil probes, while robust and useful for fast initial detection of possible degradation, are not suitable for detecting circumferential defects around the tube. One of the limitations of bobbin coils is that the eddy currents they induce are parallel to the crack orientation. Rotating probes provide a C-Scan image of the tube wall with high resolution, offering superior ability to characterize and size defects. These probes are also sensitive to circumferential defects. Moreover, they use a helical, mechanical scan process that is time-consuming and prone to additional probe wear. Further still, the complexity associated with the mechanical system for rotating the probe can contribute to poor reliability. Array probes are another conventional probe type. These probes are capable of providing information relating to the angular location of defects. The advantages associated with the use of these probes include high inspection speed and resolution. But array probes rely on sophisticated excitation and post-processing schemes. The signal from these probes is commonly contaminated by noise induced by probe vibration.

There is a need for an eddy current probe able to overcome the foregoing deficiencies and provide accurate defect detection over an entire circumference of a vessel with high inspection speed and resolution.

SUMMARY OF THE INVENTION

The present techniques present a rotating field probe design that includes three (or more) windings that work in both transmit and receive mode, to form an eddy current detection transceiver. In a transmit mode, the windings are driven with a drive signal (e.g., an alternating current) having similar or the same magnitude at each winding, but differing in phase from one another. The result is a rotating magnetic field propagating in a vessel to detect defects, such as those caused by corrosion, intergranular stress corrosion cracking, fretting, and the like. In a receive mode, the terminal voltages of the three phase windings may be measured and summed to determine the location of a defect. In this way, the probe design can be operational without using a bobbin coil to detect the defect. The probe is robust and relatively insensitive to lift-off and probe wobble.

In accordance with an embodiment, eddy current detection assembly comprises: a probe comprising three winding coil conducting elements, each spaced 120° from one another, and the three winding coil conducting elements centered on a longitudinal axis, each of the three winding coil conducting elements having a first portion extending longitudinally along the axis and a second portion extending orthogonally to the axis; an electrical signal controller coupled to the three winding coil conducting elements and configured (i) to provide a current to each of the three winding coil conducting elements and configured to provide to each of the three winding coil conducting elements a current of the same magnitude and that is 120° out of phase with respect to the current provided to each other of the three winding coil conducting elements, and to thereby produce a rotating magnetic field at a rate of rotation dependent upon a frequency of the current provided to the coils and that rotates circularly over an outer circumferential detection region, and (ii) to sense a change in load experienced by the coils when the probe is in position within a conducting vessel for examination, the change in load indicating the presence of a defect, also termed herein a flaw, in the conducting vessel over the detection region.

DETAILED DESCRIPTION

The present techniques provide a defect detection probe that can be used in high risk and yet critically important environments, such as for inspecting nuclear power plant steam generator tubes. Specifically, eddy current probes are designed to produce a rotating field that is capable of detecting defects circumferentially around the inside of a generator tube, or similar vessel, no matter the angular position of those defects and no matter whether those defects are oriented primarily longitudinally along a vessel axis (axially orientation) or tangentially along a right-angle path (circumferential orientation) to that longitudinal axis.

Figure 1A:
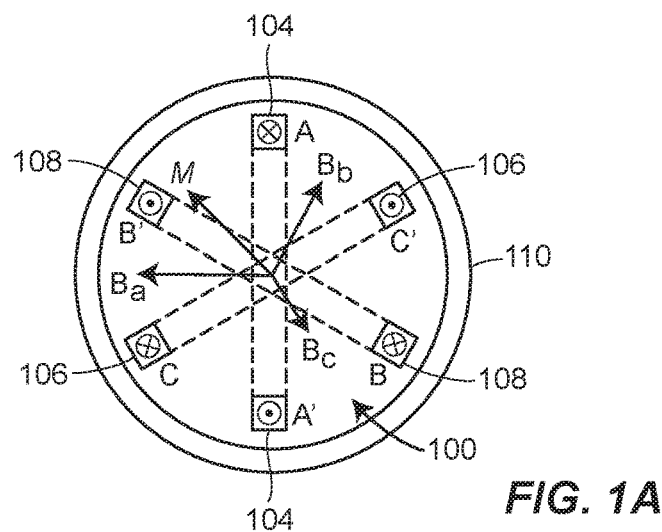
FIG. 1A is a front-end view of a three-winding coil assembly head for an eddy current in accordance with an example.
Figure 1B:
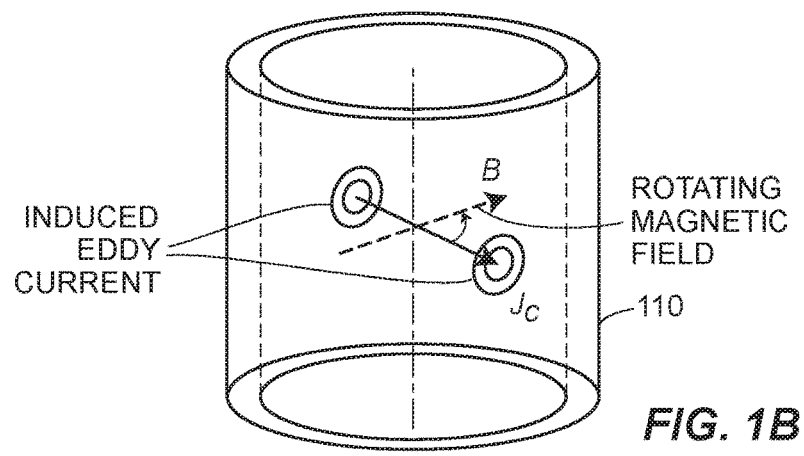
FIG. 1B is a perspective view of a vessel in which rotating magnetic fields have been induced by the device of FIG. 1A.
Figure 1C:
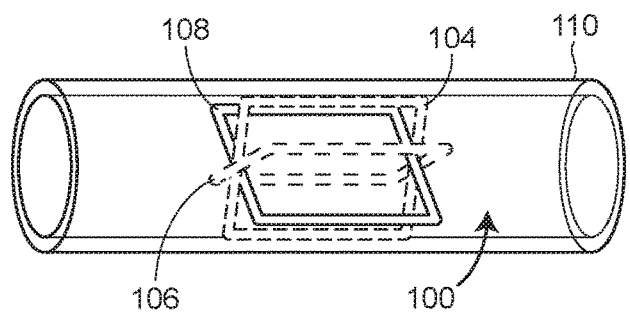
FIG. 1C is a side view showing the three-winding coil assembly head deployed within the vessel for inspection.

FIGS. 1A, 1B, and 1C illustrate an assembly head 100 for an eddy current probe. The assembly head 100 is formed of a three winding coils, 104, 106, and 108 that are each conductive and supplied with drive current signals that are nominally 120° apart in phase. In response to the drive signals, the winding coils 104-108 produce a rotating magnetic field in a vessel 110 surrounding the probe. Because of the design of the assembly head 100 that magnetic field is able to produce and detect eddy currents at any given circumferential point of the vessel, as well as extending a distance long a longitudinal axis of the vessel 110 and head 100. In the illustrated examples, each winding coil is formed in a rectangular or square framed shape that defines the many turns of the winding coil.

In the illustrated example, the eddy current probe includes three identical windings 104-108 each located 120° apart on the same physical axis to form the assembly head 100. Each of the windings is driven by a three-phase sinusoidal constant current source whose frequency and amplitude can be adjusted. The currents in the three windings 104-108 may be identical in amplitude, but 120° different in phase angle. As a result the windings 104-108, formed of coils, generate magnetic fields that rotate with time, similar to those found in a three-phase induction motor. The magnetic field generated by the three phase currents is sinusoidal in space and time. A top view of three phase excitation coils looking along the axis of the probe is shown in FIG. 1A. FIG. 1C illustrates the probe head 100 within a vessel under inspection.

Figure 2:
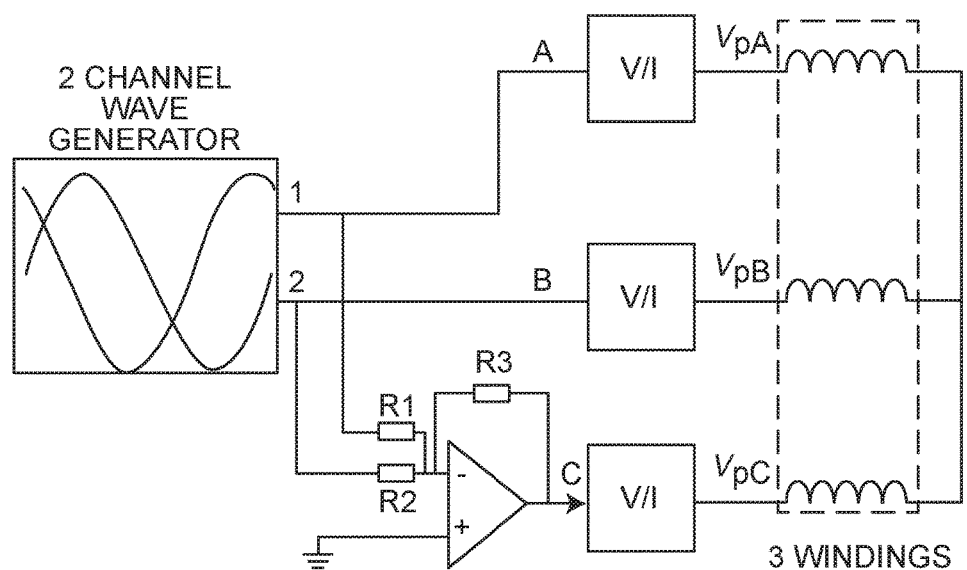
FIG. 2 is a control circuit for controlling operation of an eddy current detector probe, in accordance with an example

FIG. 2 illustrates a control circuit 200 for controlling operation of the eddy current detector probe in accordance with an example. A two channel voltage generator supplies out-of-phase signals on lines A and B to two different voltage-to-current transforms (V/I) each feeding a respective winding coil of a three winding probe (3 windings). A third channel, on line C, is formed by taking the difference between the two generated voltage signals, A and B. Each of the signals on lines A, B, and C will be of different phase (e.g., 120° apart). The signals will have the same nominal magnitudes. Furthermore, for probe heads with greater than three windings, the controller will generate greater than three different control signals, each phase separated.

The control circuit detects defects from the probe using three asymmetric phase voltages, $\nabla_{pA}$, $\nabla_{pB}$ and $\nabla_{pC}$. A schematic of the three-phase excitation system is shown in FIG. 2, where the probe scans the vessel along the circumferentially and extending along the axial direction, as shown in FIG. 1C.

The vector sum of the three phase voltages is equal to zero when all conditions are symmetric. However, the presence of a defect in the tube wall unbalances the system, as presented in equation (1).

$$\overline{V}_{sum} = \overline{V}_{pA} + \overline{V}_{pB} + \overline{V}_{pC} = \begin{cases} = 0 & \text{when } Z_A = Z_B = Z_C \\ \neq 0 & \text{otherwise} \end{cases} \quad (1)$$

where $\overline{V}_{pX} = \overline{I}_{pX} * Z_{lx}$.

A defect will result in an imbalance in the terminal voltage in the three windings resulting in non-zero $\nabla_{sum}$. The control circuit 200 detects that imbalance and determines a coordinate location of the imbalance based on the phase differences on the pick-up (i.e., receiver) signals by the windings.

Figure 3A:
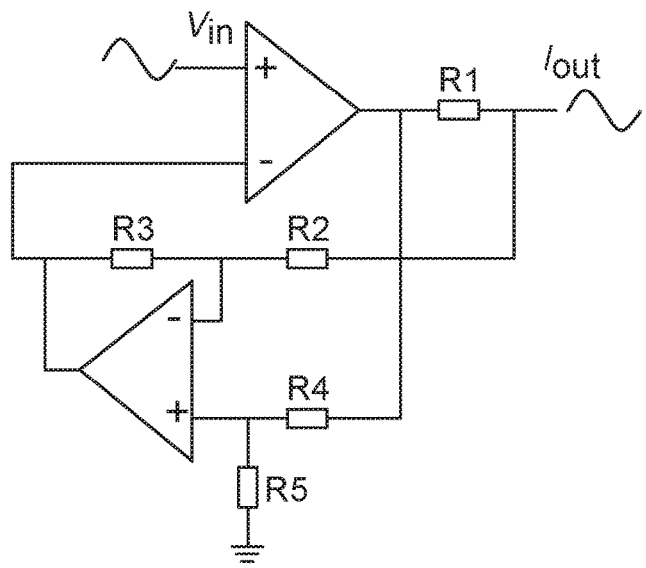
FIG. 3A illustrates a voltage controlled constant current circuit, in accordance with an example.

An example probe with three phase windings was designed according to the following. A 3-phase current source and signal conditioning circuit was designed, built and tested, along with a two-channel function generator, as in FIG. 2. The circuit was used to generate the excitation signals. The two (2) excitation signals are identical in amplitude but 120° apart in phase. In this particular example, the third phase was generated from these two signals by summing them and inverting the result. The voltage controlled constant current circuit is shown in FIG. 3A, where the resistances R2=R3=R4=R5. The output current $$I_{out} = \frac{V_{in}}{R1}.$$

The output frequency can be varied from 100 Hz to 100 kHz.

Figure 3B:
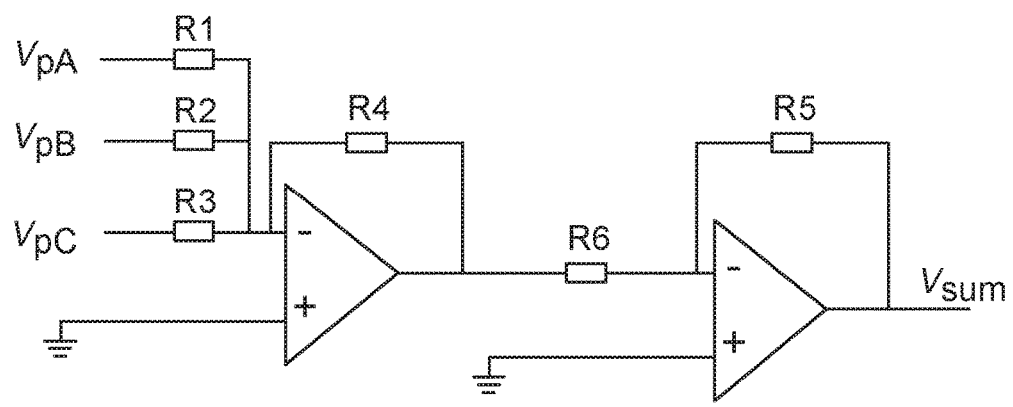
FIG. 3B illustrates a voltage summing circuit that receives three terminal phase voltages from the eddy current detector, in accordance with an example.

The three terminal phase voltages were added using the circuit presented in FIG. 3B, where R1=R2=R3=R4. The output of the circuit Vsum is given by equation (2).

$$Vsum = \frac{R_6}{R_5}(VpA + VpB + VpC) \quad (2)$$

In this example, the three windings employ an identical number of turns. The three DC resistances were measured and found to be 23Ω, 24.7Ω, and 25.5Ω, separately. A lock-in amplifier was used to recover the baseband signal and improve the signal-to-noise ratio. It will be understood that further signal improvement techniques may be used in other examples.

The circuits in FIGS. 2, 3A, and 3B may be formed within a single controller for the eddy current probe device. That controller may be implemented in hardware, software, firmware, or some combination thereof. That controller forms an electrical signal controller Thus, the electrical signal controller may include a voltage signal generator, feeding a current source, a separate current source generator, a phase modification stage, and voltage detection stage to detect variations in different windings. The controller may include a detection circuit coupled to the electrical signal controller and configured to determine a circumferential position a defect within a vessel. The controller may include an axial position sensor coupled to the detection circuit to determine an axial position of the defect in the conducting vessel. Additionally, the controller may be coupled to a translation stage that moves the probe device within a vessel for detecting the defect. The controller, in some examples, controls that translation stage using a feedback of the defect detection signal developed from the voltages detected on the probe. That feedback signal may be used for fine and/or course movement adjustments in different examples described herein.

Thus, we have shown a rotating transceiver eddy current probe for the inspection of tubes or other vessels. The probe employs a rotating electromagnetic field without the need for mechanically rotating the coils, i.e., windings. The probe is able to measure for defects at any point along a vessel through measurements of impedance changes in coils. In this way, the transceiver set up need not employ a bobbin coil, but is able to achieve high inspection speed since it does not involve mechanical rotation.

The probe is sensitive to defects of all orientations. Furthermore, the circumferential position of a defect can be inferred from the phase of the probe output. Initial results demonstrate that the probe can be used for detecting defects in steam generator tubes in nuclear power plants.

Figure 4:
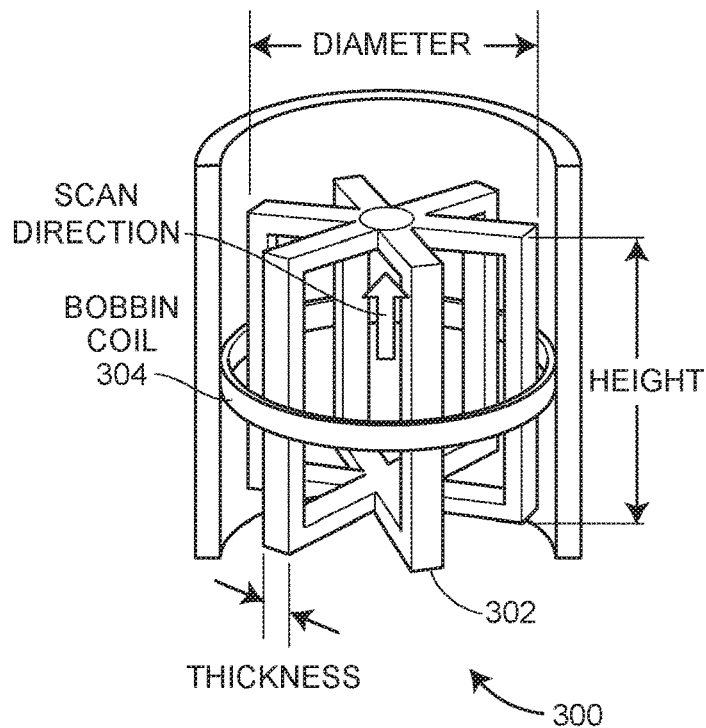
FIG. 4 illustrates another example of eddy current detection probe, having a three winding coil assembly head and a bobbin coil, in accordance with an example.

FIG. 4 illustrates another example of an eddy current detection probe, in the form of a dual body device 300 having probe head 302 formed of windings like those described hereinabove, and including a bobbin coil 304 surrounding the probe head 302. Specifically, the bobbin coil 304 surrounds the three winding coil, conducting elements of the probe head and provides a second eddy current sensor. The optional bobbin coil 304 can provide a signal that is used by a controller to fine-tune the defect measurement from the probe head 302. For example, a controller electrically connect to the probe head 302 and the bobbin coil 304 may use the signal received from the bobbin coil 304 to initiate measurements of the signal from the probe head 302 to limit the data capture to regions containing defects in the vessel wall as the device 300 is moving along the longitudinal axis (in the direction of the arrow as shown). That is, as the probe head 302 and bobbin coil 304 are moved in a scan direction, the controller may keep the probe head 302 in a non-scan mode, until a signal measured from the bobbin coil 304 is such that the controller determines the probe head 302 should begin taking measurements. The bobbin coil 304 signal could also be used to increase the data collection rate to obtain a finer scan of the defect region whilst maintaining a coarser scan of other regions. This will lead to a finer measurement and a more precise location of the defect. In this way, the speed and precision of the device 300 may be even further increased through selective switching between sensors using the device controller.

Figure 5:
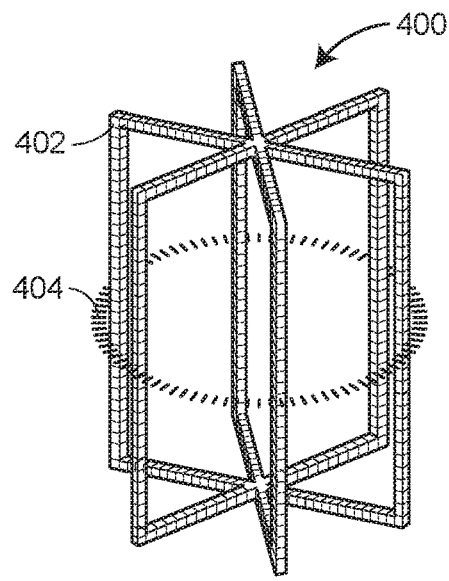
FIG. 5 illustrates another example of eddy current detection probe, having a three winding coil assembly head and a giant magnetoresistance (GMR) sensor, in accordance with an example.

FIG. 5 illustrates another example of an eddy current detection probe similar to that of FIG. 4 and having a dual body device 400 having probe head 402 formed of windings like those described hereinabove. Instead of a bobbin coil surrounding the probe head 402, a giant magnetoresistance (GMR) sensor 404 formed a ring of miniature sensor elements surrounds the probe head 402. The GMR sensor 404 can provided similar functionality to the bobbin coil 304, that is, working with a controller to determine when to engage the probe head 402 to take measurements, i.e., when to begin providing the supply voltages to each of the three winding coils.

The GMR sensor exhibits a quantum mechanical magnetoresistance effect and is formed of thin-film structures composed of alternating ferromagnetic and non-magnetic conductive layers. In other examples, the GMR sensor 404 may be replaced by a sensitive Hall Effect sensor.

Figure 6:
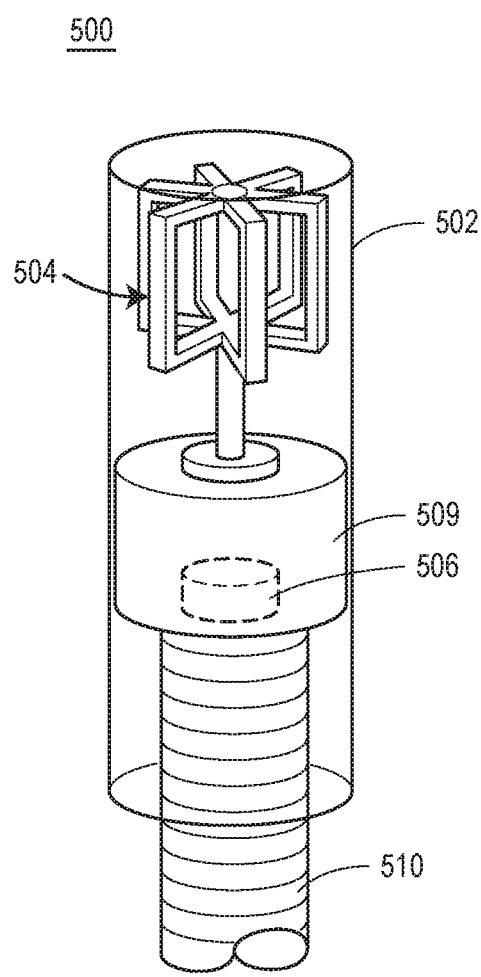
FIG. 6 illustrates an example eddy current detection assembly having a housing surrounding a probe head and having a position control stage, in accordance with an example.

FIG. 6 illustrates an eddy current detection assembly 500 having a housing 502 surrounds a probe head 504 having three winding coil conducting elements, disposed adjacent an inner wall of the housing 502. An electrical signal controller 506 is positioned within the housing 502 and is electrically connected to the probe head 504 through electrical connections in a coupler housing 508. While not shown, the electrical signal controller 506 includes one or more processors and one or more computer readable storage mediums storing instructions executable by the one or more processors. The controller 506 is contained within a controller housing 509 within the housing 502 to allow for electrical isolation and also to provide support based for the probe head 504. The controller housing 509 is mounted to a position control stage 510 that is able to move the probe head 504 (and the entire housing 502) along an axial direction of a vessel under examination, to sense for defects in the vessel. The position control stage 510 may be an electronically controllable piston-based stage, for example.

Figure 7:
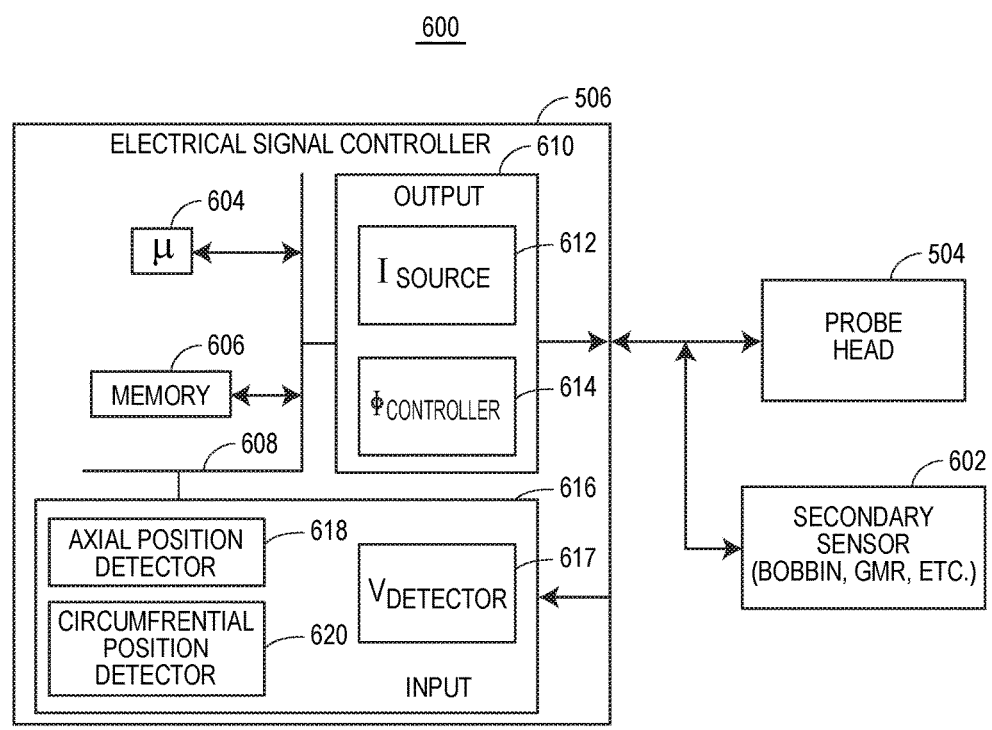
FIG. 7 illustrates an example controller for the eddy current detection assembly of FIG. 6, in accordance with an example.

FIG. 7 is a control schematic 600 of the assembly 500, further showing a second sensor 602. The probe head 504 and the secondary sensor 602 are both coupled to the controller 506, which includes a microprocessor 604 and a memory 606, which are both connected to a communication bus 608. A first stage 610, acting as an output drive stage, includes a current source 612 to provide currents to drive the winding elements of the probe head 504. The first stage 610 further includes a phase controller 614 to adjust the phase on the currents generated by the current source 612 to drive the probe head 504. A second stage 616, acting as an input receiver stage, includes a voltage detection circuit 617, an axial position detector 618, and a circumferential position detector 620 that collect data from the probe head 504 (and in some examples, additionally from dedicated secondary sensors 602) and determine the voltages on each probe winding and the axial position and circumferential positions of defects detected in a vessel.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

Unless specifically stated otherwise, discussions herein using words such as "processing," "computing," "calculating," "determining," "presenting," "displaying," or the like may refer to actions or processes of a machine (e.g., a computer or other device having one or more processors) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

This detailed description is to be construed as an example only and does not describe every possible embodiment, as describing every possible embodiment would be impractical, if not impossible. One could implement numerous alternate embodiments, using either current technology or technology developed after the filing date of this application.

What is claimed:

1. An eddy current detection assembly comprising:
   a probe comprising three winding coil conducting elements, each spaced 120° from one another, and the three winding coil conducting elements centered on a longitudinal axis, each of the three winding coil conducting elements having a first portion extending longitudinally along the axis and a second portion extending orthogonally to the axis; and
   an electrical signal controller coupled to the three winding coil conducting elements and configured
   (i) to provide a current to each of the three winding coil conducting elements and configured to provide to each of the three winding coil conducting elements a current of the same magnitude and that is 120° out of phase with respect to the current provided to each other of the three winding coil conducting elements, and to thereby produce a rotating magnetic field at a rate of rotation dependent upon a frequency of the current provided to the coils and that rotates circularly over an outer circumferential detection region, and
   (ii) to sense a change in load experienced by the coils when the probe is in position within a conducting vessel for examination, the change in load indicating the presence of a defect in the conducting vessel over the detection region; and
   wherein the electrical signal controller is a transceiver and comprises;
   a current source coupled to the three winding coil conducting elements, the current source configured to produce an alternating current at a frequency from 0.1 kHz to 100 kHz;
   a phase modification stage configured to receive the alternating current and to supply an alternating current to each of the three winding coil conducting elements with a phase difference of 120°; and
   a voltage detection stage coupled to detect a voltage on each of the three winding coil conducting elements and configured to sum the detected voltages, wherein the summation of the detected voltages indicates the presence of the defect when the value of the summation of the detected voltages is above a threshold value.

2. The assembly of claim 1, further comprising a probe housing deployable within the conducting vessel and containing the three winding coil conducting elements.

3. The assembly of claim 2, wherein the electrical signal controller is contained within the probe housing.

4. The assembly of claim 1, further comprising a detection circuit coupled to the electrical signal controller and configured to determine a circumferential position of the Eddy current in the conducting vessel.

5. The assembly of claim 4, further comprising an axial position sensor, wherein the detection circuit is coupled to the axial position sensor to determine an axial position of the defect in the conducting vessel.

6. The assembly of claim 1, further comprising a bobbin coil sensor surrounding the three winding coil conducting elements and providing a second Eddy current sensor.

7. The assembly of claim 1, further comprising a giant magnetoresistance (GMR) sensor surrounding the three winding coil conducting elements and providing a second Eddy current sensor.

8. The assembly of claim 1, further comprising a position control element configured to move the probe along an axial direction of the conducting vessel, such that the assembly senses for defects at different axial and circumferential positions within the conducting vessel.

9. The assembly of claim 1, wherein the threshold value is set at an appropriate level slightly above zero volts.

* * * * *